US011453856B2

(12) United States Patent
Stroeman et al.

(10) Patent No.: US 11,453,856 B2
(45) Date of Patent: Sep. 27, 2022

(54) LACTOBACILLUS CURVATUS STRAINS USEFUL FOR INHIBITION OF LISTERIA

(71) Applicant: CHR. HANSEN A/S, Hoersholm (DK)

(72) Inventors: Per Stroeman, Hoersholm (DK); Christian Elmshaeuser, Pohlheim (DE); Kim Ib Soerensen, Hoersholm (DK); Tim Martin Seibert, Pohlheim (DE); Rute Neves, Hoersholm (DK)

(73) Assignee: CHR. HANSEN A/S, Hoersholm (DK)

( * ) Notice: Subject to any disclaimer, the term of this patent is extended or adjusted under 35 U.S.C. 154(b) by 139 days.

(21) Appl. No.: 16/643,350

(22) PCT Filed: Aug. 29, 2018

(86) PCT No.: PCT/EP2018/073227
§ 371 (c)(1),
(2) Date: Feb. 28, 2020

(87) PCT Pub. No.: WO2019/043055
PCT Pub. Date: Mar. 7, 2019

(65) Prior Publication Data
US 2021/0227834 A1 Jul. 29, 2021

(30) Foreign Application Priority Data
Aug. 31, 2017 (EP) .................................... 17188899

(51) Int. Cl.
*C12N 1/20* (2006.01)
*A01N 63/20* (2020.01)
*A23B 4/22* (2006.01)
*A23L 3/3571* (2006.01)
*C12R 1/225* (2006.01)

(52) U.S. Cl.
CPC ............... *C12N 1/20* (2013.01); *A01N 63/20* (2020.01); *A23B 4/22* (2013.01); *A23L 3/3571* (2013.01); *C12N 1/205* (2021.05); *A23V 2002/00* (2013.01); *A23Y 2220/25* (2013.01); *C12R 2001/225* (2021.05)

(58) Field of Classification Search
CPC .......... C12N 1/20; C12N 1/205; A01N 63/20; A23B 4/22; A23L 3/3571; C12R 2001/225; A23V 2002/00; A23Y 2220/25

USPC ........................................................... 426/61
See application file for complete search history.

(56) References Cited

U.S. PATENT DOCUMENTS

| 8,697,422 | B2 | 4/2014 | Stahnke et al. | |
| 9,468,231 | B2 | 10/2016 | Stahnke et al. | |
| 2010/0086968 | A1* | 4/2010 | Stahnke | A23B 4/22 435/69.1 |
| 2019/0029279 | A1 | 1/2019 | Erkes et al. | |

FOREIGN PATENT DOCUMENTS

| WO | WO-2008/113781 | 9/2008 |
| WO | WO-2016/128508 | 8/2016 |

OTHER PUBLICATIONS

Fielding, L. M. et al. 1997. Int. J. Food Micobiol. 35: 259-265 (Year: 1997).*
Castellano et al., "Strategies for Pathogen Biocontrol Using Lactic Acid Bacteria and Their Metabolites: A Focus on Meat Ecosystems and Industrial Environments," Microorganisms, vol. 5, No. 38, 26 pages (Jul. 2017).
Messens et al., "Modelling growth and bacteriocin production by *Lactobacillus curvatus* LTH 1174 in response to temperature and pH values used for European sausage fermentation processes," International Journal of Food Microbiology, vol. 81, Feb. 2003, pp. 41-52.

* cited by examiner

*Primary Examiner* — Hamid R Badr
(74) *Attorney, Agent, or Firm* — Foley & Lardner LLP

(57) ABSTRACT

The *Lactobacillus curvatus* strain deposited as DSM18775 is used as a biopreservative culture in a wide range of meat products due to its production of bacteriocin. The present invention relates to *Lactobacillus curvatus* strains having an extended lag phase of at least 24 hours at 30° C. relative to DSM18775. In a presently preferred embodiment, the strains are mutants of DSM18775, such as the *Lactobacillus curvatus* strain deposited as DSM32590 and the *Lactobacillus curvatus* strain deposited as DSM 32591. Further, the invention relates to a method for inhibiting *Listeria* in a food product comprising adding bacteria of a *Lactobacillus curvatus* strain according to the invention to a food product in a concentration of at least $10^5$ CFU/g.

17 Claims, 5 Drawing Sheets

LACTOBACILLUS CURVATUS STRAINS USEFUL FOR INHIBITION OF LISTERIA

CROSS-REFERENCE TO RELATED APPLICATIONS

The present application is the U.S. National Stage of International Application No. PCT/EP2018/073227, filed Aug. 29, 2018, and claims priority to European Patent Application No. 17188899.3, filed Aug. 31, 2017.

FIELD OF THE INVENTION

The *Lactobacillus curvatus* strain deposited as DSM 18775 is used as a biopreservative culture in a wide range of meat products due to its production of bacteriocin.

The present invention relates to *Lactobacillus curvatus* strains having an extended lag phase of at least 24 hours at 30° C. relative to DSM 18775. In a presently preferred embodiment, the strains are mutants of DSM 18775, such as the *Lactobacillus curvatus* strain deposited as DSM 32590 (TpG3) and the *Lactobacillus curvatus* strain deposited as DSM 32591 (TpG57).

Further, the invention relates to a method for inhibiting *Listeria* in a food product comprising adding bacteria of a *Lactobacillus curvatus* strain according to the invention to a food product in a concentration of at least $10^5$ CFU/g.

BACKGROUND OF THE INVENTION

*Lactobacillus curvatus* is probably the most common *lactobacillus* species reported from fermented meat products and known for its potential usage in food preservation due to the production of antimicrobial components or peptides. Most of these inhibitory peptides are a type of bacteriocins that belong to the Class II lantibiotics and where some are listed under the name of curvacin, and other under collective name sakasin P or G, or sakasin X, T or P. The mode of action is primarily due to altering the permeability barrier of the cell membrane and thereby dissipation or collapse of the ion transport force system inside and outside of the cell of the spoilage bacteria. The bacteriocins work primarily against other closely related Gram-positive species, but cell extracts isolated from some *Lactobacillus curvatus* strains have also been shown to have an antimicrobial effect against Gram-negative bacteria.

The *Lactobacillus curvatus* strain deposited as DSM 18775 produces a bacteriocin that display bactericidal mode of action towards other Gram-positive strains which has made this strain important for protection against spoilage bacteria in the meat industry.

SUMMARY OF THE INVENTION

Ideally, a culture for meat protection should demonstrate limited growth at the temperature of the respective application and a sufficient production of bacteriocin to limit growth of spoilage bacteria, such as *Listeria* spp. In addition, the culture should not produce off-flavors or demonstrate a high acidification rate when spread onto (cooked) meat products.

The present invention relates to *Lactobacillus curvatus* strains which have an extended lag phase at 30° C. for at least 24 hours relative to DSM 18775.

Figure 1:
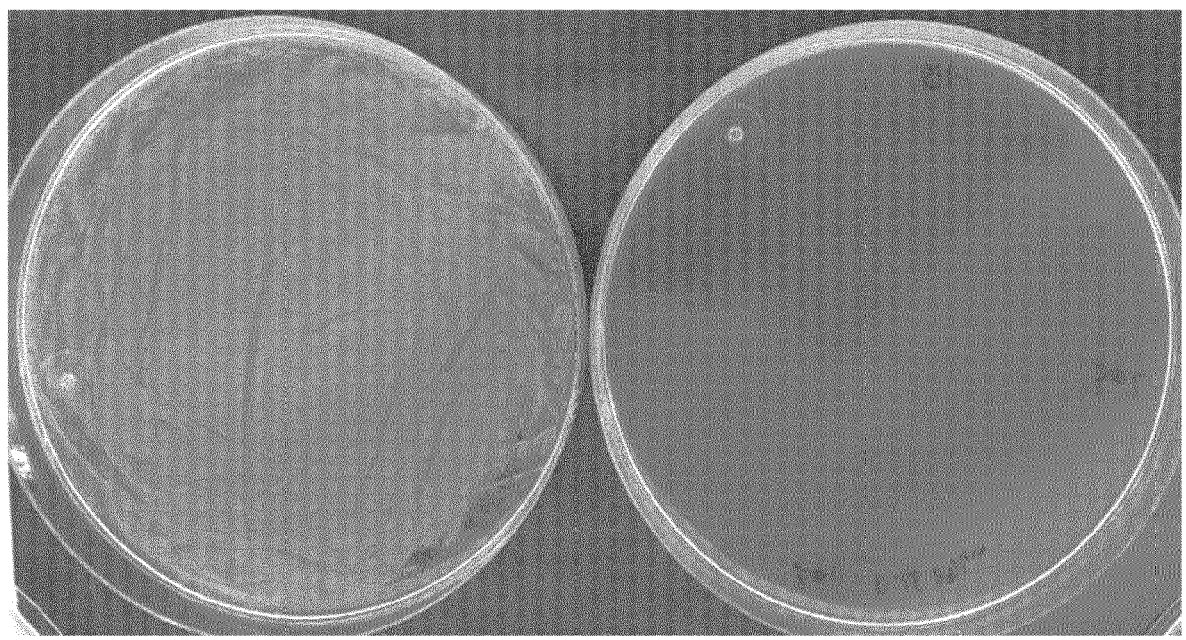

Presently preferred strains of the invention are mutants of the *Lactobacillus curvatus* strain DSM18775. The development of two mutants is described in detail in the examples. After eight weeks of cell-transfer every other day and a total of four UV-treatments, a screening of approximately 4,000 isolates resulted in a slow growing mutant, TpG3, with an extended lag phase of 24 hours relative to the mother strain when incubated at 30° C. (FIG. 1). The production of the antimicrobial agent, bacteriocin, is given for the mutant TpG3 in Table 1.

An additional round of Adaptive Laboratory Evolution (ALE) with the mutant TpG3 was performed over a period of 2 weeks at 15° C. with cell transfer every other day including one UV treatment. This resulted in isolation of a further isolate TpG57, with a substantially extended lag-phase of more than 48 hours relative to the wild type *Lactobacillus curvatus* DSM 18775. Production of bacteriocin was verified by plate assays with *Micrococcus luteus* DSM 1790 and was shown to be comparable with the antimicrobial bacteriocin production of TpG3.

It was surprisingly found that these two mutants do not grow during the lag phase but were nevertheless metabolically active and even had an anti-listerial effect that was about 64-fold higher compared to the mother strain when grown under the same conditions at 20° C.

Figure 2:
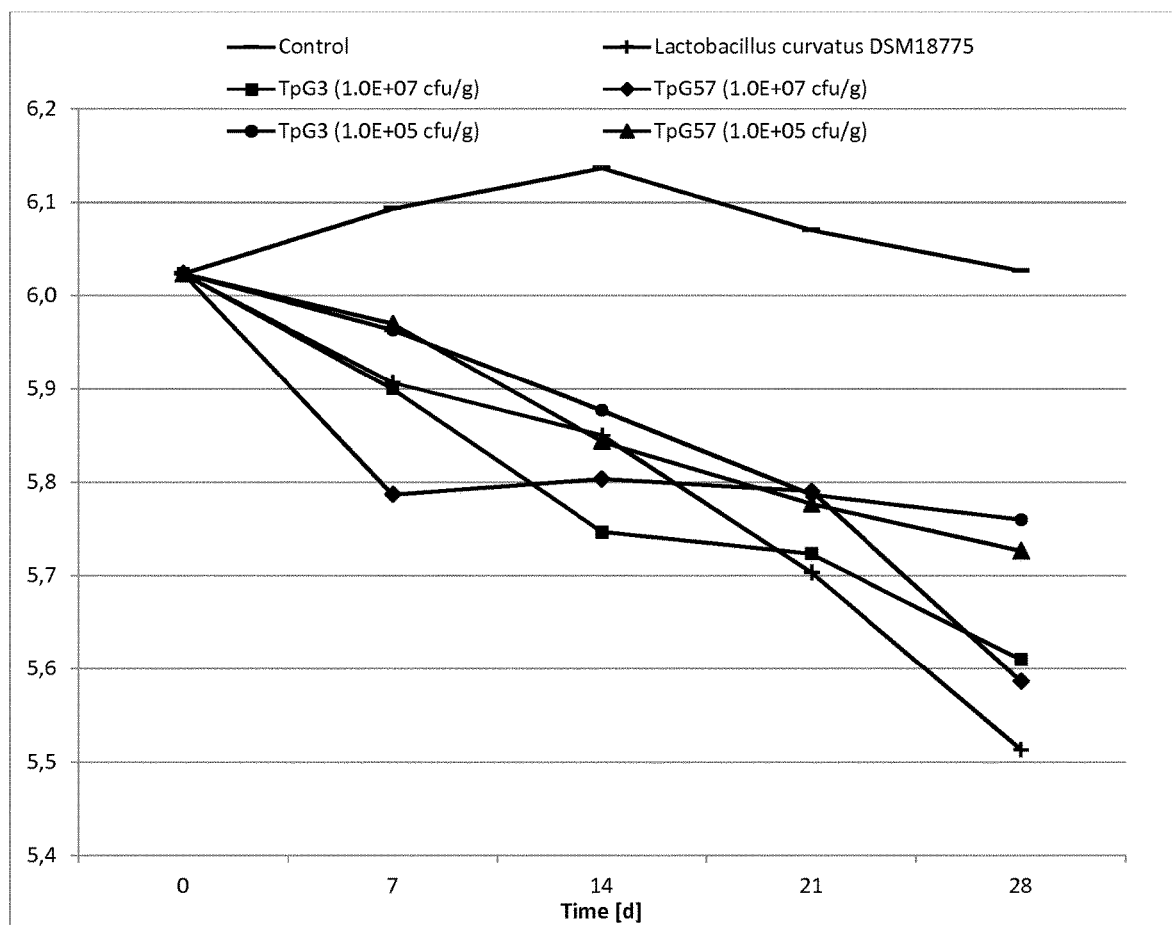
Figure 3:
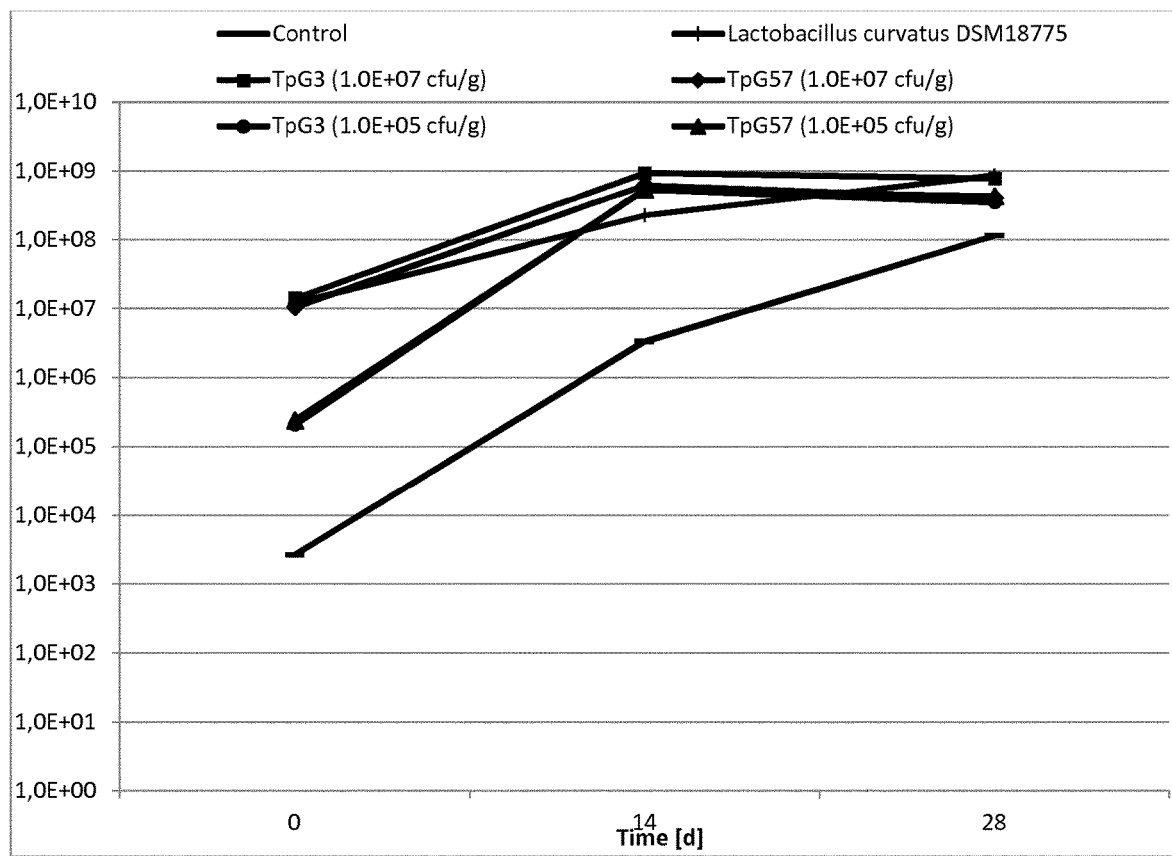
Figure 4:
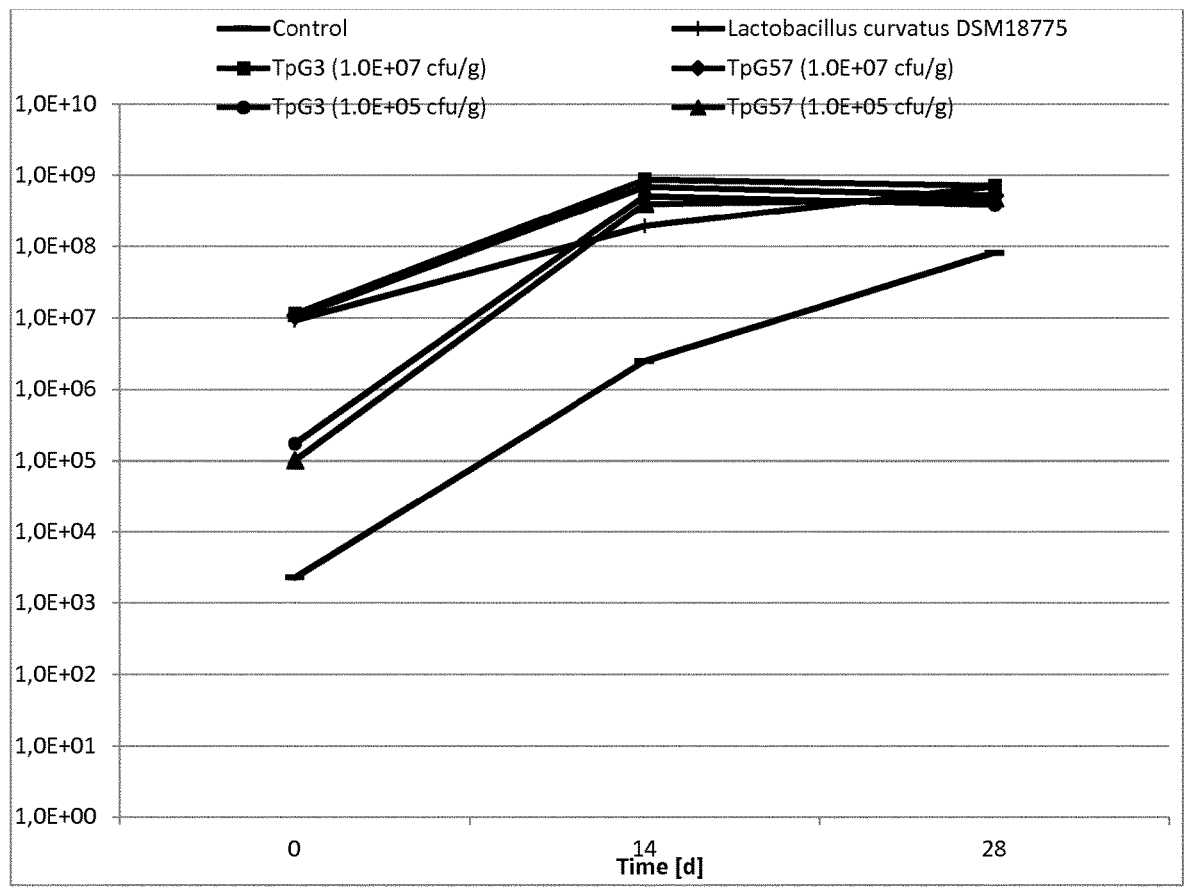

Application trials have demonstrated that both mutants were able to inhibit the growth of *Listeria* to the same extent as DSM 18775 and that the samples of ham inoculated with a cell count of 1.0E+05 cfu/g of TpG3 and TpG57 were significantly better in regard to smell and taste (no acidic flavor) than the samples of ham inoculated with a cell count of 1.0E+07 cfu/g of TpG3 and TpG57 and the samples inoculated with DSM 18775 (Table 2). The mutant strains TpG3 and TpG57 had a slower pH drop and a higher pH value at the end of shelf life (FIG. 2).

Thus, the *Lactobacillus curvatus* strain deposited as DSM 32590 (TpG3) and the *Lactobacillus curvatus* strain deposited as DSM 32591 (TpG57) may be even more useful for biopreservation of food products than strain DSM 18775 from which they have been derived.

DETAILED DISCLOSURE OF THE INVENTION

Bacterial contamination of food products is known to be responsible for the transmission of food borne illness. This problem is particularly important in meat and dairy products which are not reheated by consumers prior to ingestion and which are stored for extended times in refrigerators at 2-10° C. This storage period is often termed the "shelf life". As used herein the term "shelf life" means the period of time that a food product remains saleable to retail customers. In traditional meat processing, the shelf life of meat and meat by-products is about 30 to 40 days after an animal has been slaughtered. Refrigeration of meat during this period of time is expected to largely arrest and/or retard the growth of pathogenic bacteria, and to a lesser extent, spoilage bacteria. After about 30 to 40 days, however, refrigeration is no longer able to effectively control the proliferation of spoilage bacteria below acceptable levels.

The strains of the present invention are particularly useful for storage, fermenting, ripening or curing of the food product which takes place at a temperature of from 2° C. to 45° C., such as at a temperature of from 10° C. to 30° C., such as at a temperature of from 10° C. to 25° C. The storage, fermenting, ripening or curing of the food product may last for from 8 hours to several days/weeks.

Lactic acid bacterial strain(s) added to food to inhibit pathogens as well as spoilage bacteria and/or extend shelf life without changing the sensory properties of the product are termed "bioprotective cultures". Protective cultures are not intended to change the sensory properties of the product.

Their use or that of their metabolic products (organic acids, hydrogen peroxide, enzymes and bacteriocins) is often referred to as "bioprotection". In the present context the term "bioprotective culture" and composition of the invention are used interchangeably unless the context indicates otherwise.

An important aspect in the evaluation of the use of a strain as a bioprotective culture is the ability of the strain to work in the food product for which it is intended. In this respect it is not only important that the strain is able to inhibit any undesired food-borne pathogenic or spoilage bacteria in the product under relevant storage conditions, but also that it does not produce any undesired sensory effects (off-taste, off-odors or unwanted color changes).

The manufacturing of a fermented food product is often being controlled and performed by a starter culture. The starter culture is responsible for the development of a non-limiting group of quality parameters such as acidification, reduction in water binding and water activity, general appearance, color, texture, odor, aroma, taste, flavor and other sensorial and technological parameters. Thus, minimal, or preferably no, influence on the quality parameters from the bioprotective culture is to be provided.

Starter cultures for meat fermentation are commonly comprised by one or more lactic acid bacteria. Typically, a starter culture will proliferate during the fermentation process. During the fermentation process the lactic acid bacteria primarily produce lactic acid whereby pH drops to the desired pH-value depending on the culture and the processing conditions (temperature, sugar type/content etc.), and importantly, the sensory properties of the product are distinctly changed to the desired aroma and flavor profile characteristic for the product.

In order to reduce the concentration of spoilage and pathogenic bacteria, it is desired that this reduction can be provided without significantly altering the quality of the final food product, i.e. the food producer may apply the bioprotective culture to his present or preferred recipe without otherwise changing the recipe or processing conditions. To obtain the desired effect a culture of a bacteriocin-producing species may be applied to a food material as a bioprotective culture, which is separated from the starter culture. In the present context "bioprotective culture" is a culture that is added to the food material or joined with the starter culture, but which does not form part of the starter culture, i.e. the bioprotective culture is an additional culture not attempted to "produce" the fermented food product, but to supply an extra technological advantage; in this case a killing, inactivating or inhibiting effect towards pathogenic or spoilage bacteria. In the present context "bioprotective culture" and "bacteriocin-producing species" are used interchangeably unless the context indicates otherwise.

The present invention provides a method for inhibiting the amount of pathogenic and spoilage bacteria in a food product. In the present context the term "inhibiting the amount" relates to an inhibition of the amount of pathogenic and/or spoilage bacteria. An inhibition may be provided by killing, inactivating or inhibiting the growth of the spoilage or pathogenic bacteria. In an embodiment of the present invention 100% of the pathogenic and/or spoilage bacteria are killed, inactivated or inhibited, such as at least 90%, e.g. at least 75%, such as at least 50%, e.g. at least 40%, such as at least 30%, e.g. at least 25%, such as at least 20%, e.g. at least 10%, such as at least 5%, e.g. at least 1%. In a preferred embodiment, bacteria already present are eliminated or the amount reduced to an amount being below the qualitative detection limit.

The term "spoilage bacteria" as used herein refers to any type of bacteria that act to spoil food. Spoilage bacteria may grow and proliferate to such a degree that a food product is made unsuitable or undesirable for human or animal consumption. Bacteria are able to proliferate on food surfaces, such as meat surfaces, by assimilating sugars and proteins on such surfaces. By metabolizing these components, spoilage bacteria create by-products including carbon dioxide, methane, nitrogenous compounds, butyric acid, propionic acid, lactic acid, formic acid, sulfur compounds, and other undesired gases and acids. The production of such by-products alters the color of meat surfaces, often turning meat from a red color to a brown, grey or green color. Gaseous by-products generated by spoilage bacteria also give spoiled meat an undesirable odor. The color and odor alterations of meat due to the growth of spoilage bacteria on the surface of a meat product often make such food product unsalable to consumers.

In addition to the control of spoilage bacteria, another significant concern in the food processing industry is controlling the growth of food-borne pathogenic bacteria. As used herein, the term "food-borne pathogenic bacteria" refers to any food poisoning bacteria which are capable of causing disease or illness in animals or humans. The term "food-borne pathogenic bacteria" will be understood to include bacteria that infect the food product (for instance meat) and thereby cause disease or illness, as well as bacteria that produce toxins that cause disease or illness. The food-borne pathogenic bacterium to be inhibited may be one or more of the bacteria *Aeromonas caviae; Aeromonas hydrophila; Aeromonas sobria; Bacillus cereus; Campylobacter jejuni; Citrobacter* ssp.; *Clostridium botulinum; Clostridium perfringens; Enterobacter* ssp.; *Enterococcus* ssp.; *Escherichia coli* enteroinvasive strains; *Escherichia coli* enteropathogenic strains; *Escherichia coli* enterotoxigenic strains; *Escherichia coli* O157:H7; *Klebsiella* ssp.; *Listeria monocytogenes; Plesiomonas shigelloides; Salmonella* ssp.; *Shigella* ssp.; *Staphylococcus aureus; Streptococcus* ssp.; *Vibrio cholerae; Yersinia enterocolitica*. More preferably, the pathogenic-bacteria are *Listeria monocytogenes*.

The present invention provides a method for inhibiting the amount of spoilage or pathogenic bacteria in a food product comprising adding bacteria of a *Lactobacillus curvatus* strain according to the invention or a composition comprising a *Lactobacillus curvatus* strain according to the invention to a food product in a concentration of at least $10^5$ CFU/g.

A bacterial "strain" as used herein refers to a bacterium which remains genetically unchanged when grown or multiplied.

In the context of the present invention, the term "strain having an extended lag phase of at least 24 hours at 30° C. relative to DSM 18775" means that when the strain is grown under identical conditions as DSM 18775, no visible growth is seen for the strain having an extended lag phase after 24 hours under conditions where good growth is observed for DSM 18775. This can be tested on MRS agar plates as described in Example 1 and illustrated in FIG. 1. In some embodiments of the present invention, the extended lag phase is even longer such as at least 48 hours, at least 72 hours or at least 96 hours.

In the present context, the term "mutant" refers to a bacterial strain derived from the deposited strain, by means of e.g. genetic engineering, radiation and/or chemical treatment, which is a functionally equivalent mutant, i.e. a mutant that has substantially the same, or improved, properties regarding the effect on urate concentration in blood of a subject as the mother strain. The term "mutant" refers to a strain obtained by subjecting the *Lactobacillus curvatus* strain deposited as DSM 32590 or the mutant strain thereof deposited as DSM 32591 to conventional mutagenization treatment, including treatment with a chemical mutagen such as ethane methane sulphonate (EMS) or N-methyl-N'-nitro-N-nitroguanidine (NTG), UV light followed by a screening/selection step as well as to a spontaneously occurring mutant. In a presently preferred functionally equivalent mutant, less than 5%, or less than 1% or even less than 0.1% of the nucleotides in the bacterial genome have been shifted with another nucleotide, or deleted, compared to the strain deposited as *Lactobacillus curvatus* DSM 18775.

The *Lactobacillus curvatus* strains of the present invention may be useful for bioprotection of fermented as well as non-fermented food products.

Examples of fermented food products include, but are not limited to dairy products such as various cheese products, fermented meat products, such as sausages e.g. spreadable and dried sausages and ham, fermented fish and fermented vegetables.

The term "food product" as used herein refers to any food that is susceptible to bacterial growth and proliferation of pathogenic or spoilage bacteria. Such food products include, but are not limited to, meat, dairy products, vegetables, fruits, ready-to-eat products, and grains.

As used herein, the term "meat" refers to any meat product or meat by-product (including those processed) from an animal which is consumed by humans or animals, including, without limitation, meat from bovine, ovine, porcine, poultry, fish, and crustaceous seafood. Examples of fermented meat products are sausages e.g. spreadable and dried sausages, ham, and fermented fish.

The term "dairy product" is intended to include any food product made using milk or milk products, including, but not limited to, milk, yogurt, ice cream, cheese, butter, and cream.

Examples of "fruits" are grapes such as table grapes.

Examples of Ready-to-eat products (RTE) are RTE salads, e.g. fresh green-cut salads, rocket salad, carrot sticks, maize, salad toppings, chicken sticks, seafood, mixed salads, pasta salads, etc. and couscous, rice, humus, etc.

The present invention also provides a composition comprising bacteria of a *Lactobacillus curvatus* strain according to the invention. Preferably, the *Lactobacillus curvatus* strain is present in a concentration of at least $10^5$ CFU/g.

In the culture used in example 4 of the present patent application, only one bacteriocin-producing strain is present. In some embodiments, the composition comprises bacteria of the *Lactobacillus curvatus* strain as the only bacteria present in the composition.

It is contemplated, however, that more than one bacteriocin-producing strain will be useful for some applications.

Examples of bacteria producing class IIa bacteriocins are *Carnobacterium maltaromaticum*, *Carnobacterium pisicola*, *Carnobacterium divergens*, *Lactobacillus curvatus*, *Lactobacillus sakei*, *Lactobacillus plantarum*, *Lactococcus lactis*, *Leuconostoc carnosum*, *Leuconostoc gelidium*, *Pediococcus acidilactici*, *Pediococcus pentosaceus*.

Within the scope of the present invention is a composition comprising at least two class IIa bacteriocin-producing strains. If more than one strain is used, the strains preferably produce different class IIa bacteriocin(s) and/or act on different targets.

The compositions of the invention may comprise bacteria of the *Lactobacillus curvatus* strain, and bacteria of one or more of the species *Pediococcus acidilactici*, *Lactobacillus sakei*, *Lactococcus lactis*, *Leuconostoc carnosum*, *Staphylococcus carnosus*.

Preferred additional bacteriocin-producing strains are the *Lactobacillus curvatus* strain deposited as DSM 18775, the *Pediococcus acidilactici* strain deposited as DSM 28307, the *Lactobacillus sakei* deposited as DSM 14022, the *Lactococcus lactis* strain deposited as DSM 11037, and *Leuconostoc carnosum* LC1043 available from the Danish Meat Research Institute.

In presently preferred embodiments, the composition comprises a *Lactobacillus curvatus* strain of the invention and the *Pediococcus acidilactici* strain deposited as DSM 28307, a *Lactobacillus curvatus* strain of the invention and the *Lactobacillus sakei* deposited as DSM 14022, a *Lactobacillus curvatus* strain of the invention and the *Lactococcus lactis* strain deposited as DSM 11037, or a *Lactobacillus curvatus* strain of the invention and the *Leuconostoc carnosum* LC1043.

In a further embodiment, the composition may comprise at least three class IIa bacteriocin-producing strains. Preferably, one of them will be a *Lactobacillus curvatus* strain according to the invention, the *Pediococcus acidilactici* strain deposited as DSM 28307, and *Leuconostoc* carnosum LC1043.

In a yet further embodiment, the culture comprises four or more class IIa bacteriocin-producing strains. Preferably, one of them will be a *Lactobacillus curvatus* strain according to the invention, the *Pediococcus acidilactici* strain deposited as DSM 28307, or both.

As explained above it is well-known to use lactic acid bacteria to induce fermentation of food products, typically raw salted meat products, for providing the desired change in the characteristics of the food matrix during fermentation (e.g. a desired acidification, and certain other sensory and technological parameters). During the fermentation process the lactic acid bacteria primarily produce lactic acid whereby pH drops to the desired pH-value depending on the strain(s) and the processing conditions (temperature, sugar type/content etc.), and importantly, the sensory properties of the product are distinctly changed.

As used herein, the term "fermentation" refers to the process of biochemical changes e.g. an acidification in animal and/or plant material (i.e. a food matrix), involving activity of live microbial cells under aerobic and/or anaerobic conditions to obtain a food product of desired quality.

The term "ripening" refers to the maturation, drying, flavor development, enzymatic activity like lipolysis or proteolysis leading to complex flavor development in particular for longer ripened products like salami.

If desired, the composition may in addition to the at least one bacteriocin-producing strain comprise at least one fermentation strain which assists at the least one bacteriocin-producing strain in the development of quality parameters such as acidification, reduction in water binding and water activity, general appearance, color, texture, odor, aroma, taste, flavor and other sensorial and technological parameters. Examples of such fermentation strains are *Staphylococcus carnosus* and *Staphylococcus xylosus*. For meat products with a short ripening the bacteriocin-producing strain(s) only are contemplated to be sufficient to produce an appropriate fermented meat product as also bacteriocin-producing strains are contributing to taste. However, if desired at least one *Staphylococcus* or Micrococcaceae strain could be added for taste and coloring reasons.

In presently preferred embodiments, the composition comprises a *Lactobacillus curvatus* strain of the invention, the *Pediococcus acidilactici* strain deposited as DSM 28307, and a *Staphylococcus carnosus*, a *Lactobacillus curvatus* strain of the invention, the *Lactobacillus sakei* deposited as DSM 14022 and *Staphylococcus carnosus*, a *Lactobacillus curvatus* strain of the invention—the *Lactococcus lactis* strain deposited as DSM 11037, *Staphylococcus carnosus*, or a *Lactobacillus curvatus* strain of the invention, the *Leuconostoc* carnosum LC1043 and *Staphylococcus carnosus*.

As used herein, the expression "effective amount" refers to the amount of *Lactobacillus curvatus* bacteria according to the invention which gives rise to an inhibition of the bacterial growth or a reduction of the number of other bacteria in the food product.

In a preferred embodiment of the present invention the strain or strains of the bioprotective composition is/are added in a concentration in the range of $10^2$-$10^{10}$ CFU/g product, e.g. in the range of $10^2$-$10^9$ CFU/g product, such as in the range of $10^3$-$10^9$ CFU/g product, e.g. in the range of $10^4$-$10^9$ CFU/g product, such as in the range of $10^2$-$10^8$ CFU/g product, e.g. in the range of $10^2$-$10^7$ CFU/g product, such as in the range of $10^3$-$10^7$ CFU/g product, e.g. in the range of $10^4$-$10^7$ CFU/g product, such as in the range of $10^5$-$10^7$ CFU/g product, e.g. in the range of $10^6$-$10^7$ CFU/g product such as in the range of $10^3$-$10^6$ CFU/g product, e.g. in the range of $10^3$-$10^5$ CFU/g product, such as in the range of $10^2$-$10^4$ CFU/g product for each of the strains if more than one strain. In a presently preferred embodiment, the *Lactobacillus curvatus* strain of the invention is added in a concentration of $10^5$ CFU/g product.

The present invention provides a composition of the present invention comprising bacteria of the *Lactobacillus curvatus* strains of the invention, such as the *Lactobacillus curvatus* deposited as DSM 32590 or a mutant strain thereof such as the strain deposited as DSM 32591, in dried, frozen or freeze dried form.

In one preferred embodiment, the present invention provides a composition of the present invention comprising bacteria of the *Lactobacillus curvatus* deposited as DSM 32590 and the *Lactobacillus curvatus* deposited as DSM 32591, which can be in dried, frozen or freeze dried form.

If the bacteria are freeze-dried, they are generally mixed with a cryoprotectant before they are freeze-dried in order to obtain a high viability. The term "a cryoprotectant" is used in the context of the present invention to refer to a substance that is able to improve the survival during freezing and/or drying and to improve the storage stability of bacteria. The cryoprotectant used herein preferably comprises a saccharide.

The saccharide may be a mono-, di-, oligo- or polysaccharide, or a mixture of at least two saccharides. Useful monosaccharides include glucose (also known as dextrose), fructose, ribose and galactose and useful disaccharides include among other sucrose, trehalose, maltose and lactose. The composition may comprise one or more mono- or disaccharides, such as one, two, or three or even more different saccharides.

As an example, the cryoprotectant may comprise a mixture of a disaccharide, such as sucrose, and a polysaccharide, such as maltodextrin.

The cryoprotectant may further comprise a peptide, protein, protein hydrolysate or a mixture thereof. Examples of peptides and proteins to be used are casein, pea, whey, albumin, soy protein, glutamic acid or gelatin, and any isolate or hydrolysate thereof. Other additives, e.g. antioxidants such as ascorbate, sodium citrate, propyl gallate may also be present.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language provided herein, is intended merely to better illuminate the invention and does not pose a limitation on the scope of the invention unless otherwise claimed. No language in the specification should be construed as indicating any non-claimed element as essential to the practice of the invention.

LEGEND TO FIGURES

FIG. 1

Growth performance of TpG3

Right plate, TpG3 after 24 hours incubation at 30° C.; left plate, DSM 18775 incubated under the same conditions. Inoculation was performed with equal amount of cells (200 μl: 0.25 $OD_{600}$; Petri dish diameter 14 cm).

FIG. 2 pH evolution of the cooked ham samples (n=3) during storage at +7° C.

The y-axis shows the pH. A pH drop of 0.3 units is generally considered sensorially acceptable.

FIG. 3

Total cell count in the cooked ham samples (n=3) during storage at +7° C.

The y-axis shows the total cell count in cfu/g. The detection limit is 1.0E+02 cfu/g.

FIG. 4

Lactic acid bacteria cell count in the cooked ham samples (n=3) during storage at +7° C.

The y-axis shows the lactic acid bacteria cell count in cfu/g. The detection limit is 1.0E+02 cfu/g.

FIG. 5

*Listeria* spp. cell count in the cooked ham samples (n=3) during storage at +7° C.

The y-axis shows the *Listeria* spp. cell count in cfu/g. The detection limit is 1.0E+02 cfu/g.

DEPOSIT AND EXPERT SOLUTION

The *Lactobacillus curvatus* strain TpG3 has been deposited at DSMZ (Deutsche Sammlung von Mikroorganismen und Zellkulturen GmbH, Inhoffenstrasse 7B, D-38124 Braunschweig) under the accession number DSM 32590 with a deposit date of Aug. 16, 2017 by Chr. Hansen A/S, Denmark. The deposit has been made under the conditions of the Budapest Treaty on the International Recognition of the Deposit of Microorganisms for the Purposes of Patent Procedure.

The *Lactobacillus curvatus* strain TpG57 has been deposited at DSMZ (Deutsche Sammlung von Mikroorganismen und Zellkulturen GmbH, Inhoffenstrasse 7B, D-38124 Braunschweig) under the accession number DSM 32591 with a deposit date of Aug. 16, 2017 by Chr. Hansen A/S, Denmark. The deposit has been made under the conditions of the Budapest Treaty on the International Recognition of the Deposit of Microorganisms for the Purposes of Patent Procedure.

The *Pediococcus acidilactici* strain HP has been deposited at DSMZ (Deutsche Sammlung von Mikroorganismen und Zellkulturen GmbH, Inhoffenstrasse 7B, D-38124 Braunschweig) under the accession number DSM 28307 with a deposit date of Jan. 30, 2014 by Chr. Hansen A/S, Denmark. The deposit has been made under the conditions of the Budapest Treaty on the International Recognition of the Deposit of Microorganisms for the Purposes of Patent Procedure.

The *Lactobacillus* sakei strain BJ-33 has been deposited at DSMZ (Deutsche Sammlung von Mikroorganismen und Zellkulturen GmbH, Inhoffenstrasse 7B, D-38124 Braunschweig) under the accession number DSM 14022 with a deposit date of Jan. 31, 2001 by Chr. Hansen A/S, Denmark. The deposit has been made under the conditions of the Budapest Treaty on the International Recognition of the Deposit of Microorganisms for the Purposes of Patent Procedure.

For the above-identified deposited microorganisms, the following additional indications apply:

As regards the respective Patent Offices of the respective designated states, the applicants request that a sample of the deposited microorganisms stated above only be made available to an expert nominated by the requester until the date on which the patent is granted or the date on which the application has been refused or withdrawn or is deemed to be withdrawn.

The *Lactobacillus curvatus* strain DSM 18775 is referred to in European patent EP2132297.

The *Lactococcus lactis* strain DSM 11037 is referred to in granted European patent EP928333.

The *Pediococcus acidilactici* strain DSM 10313 is referred to in European patent EP1716258.

The *Leuconostoc carnosum* LC1043 is available from the Danish Meat Research Institute or commercially available from Chr. Hansen A/S (Denmark).

The *Listeria innocua* strain Seeliger has been deposited as ATCC 33090.

The *Micrococcus luteus* strain has been deposited as DSM 1790.

Embodiments of the present invention are described below, by way of non-limiting examples.

EXAMPLES

Materials and Methods:
ALOA agar (Oxoid)
Lactobacilli MRS Broth™ (Difco)
Lactobacilli MRS Agar Agar™ (Difco)
Brain Heart Infusion (BHI) agar (Oxoid CM375)
BHI medium, Merck
Bacto™ Heart Infusion broth (BD) Difco
Microtitre plates (MTP) NUNC, Denmark
M17 agar (Oxoid)
MRS agar (Oxoid)
MRS medium (Merck)

Example 1

Inducing Mutants of *Lactobacillus curvatus* DSM 18775 Having an Extended Lag Phase at 30° C.

Adaptive Laboratory Evolution (ALE) of DSM 18775

For the ALE experiment, *Lactobacillus curvatus* cells were grown in MRS broth (10 ml) and incubated for 2×24 hours at 15° C. at which time a transfer (2%) was made to fresh MRS broth and continuous incubation at the permissive temperature 15° C. This cell transfer was repeated every 48 hours over a period of 8 weeks. Every $2^{nd}$ week along the incubation period, a sample of the cells was subjected to UV-irradiation to speed up putative temperature sensitive (TS) mutants. Instead of the 2% transfer, an aliquot of 7 ml of exponentially growing cells were diluted to 0.25 $OD_{600}$ in a Petri dish. UV mutagenesis was performed by exposing the cell layer to UV at 70 $mJ/cm^2$ for 10 min. One ml of the UV-treated cells was then transferred to 10 ml fresh MRS broth and continuously incubated at 15° C. till next transfer. At the end of the eight weeks period a sample was removed and screened for TS variants as described below.

Screening for Temperature-Sensitive Mutants of DSM 18775

Screening for temperature-sensitive (TS) mutants was carried out by plating aliquots of TS cells on MRS agar in an appropriate dilution to give approximately 150 to 200 colonies per plate after incubation at 15° C. for 3×24 hours. Single colonies were then transferred to individual wells of MTP (96 well plates) containing 100 μl fresh MRS broth and incubated for another 3×24 hours at 15° C. TS colonies were identified by replica plating into another MTP with 100 μl MRS broth and incubated aerobically for 24 hours at 30° C. at which temperature TS mutants are identified as showing growth with a longer lag phase than wild type. Screening for TS mutants was also performed by replica plating individual colonies from MTP onto MRS agar followed by aerobically incubation for 24 hours at 30° C. Finally, the TS colonies were cultured in MRS broth at 20° C.

Results

After eight weeks of transfer of *Lactobacillus curvatus* at 15° C. and four times UV-treatments approximately 4,000 mutants were screened for their inability to grow at 30° C. One such mutant, TpG3, demonstrated a reduced growth rate compared to the mother strain over a period of 24 hours at 30° C. The same reduced growth rate was observed by re-testing the putative TS strain in a bigger volume of 10 ml MRS broth over a period of 72 hours at 30° C. On MRS agar plates, no growth at all was observed after 24 hours incubation, whereas good growth was observed for DSM 18775 (FIG. 1).

Example 2

Selection of Further Mutants of *Lactobacillus curvatus* DSM 18775 Having an Extended Lag Phase at 30° C.

Second Generation Mutants Derived from TpG3

To further extend the lag phase the *Lactobacillus curvatus* DSM 18775 mutant TpG3 was selected and subjected to continuously ALE at 15° C. over a period of 2 weeks with cell transfers (2%) every other day in addition to one UV-mutagenic treatment as described under Example 1. Out of approximately 500 colonies screened, only 2 mutants were isolated showing deferred growth at 30° C. with an extended lag phase of more than 48 hours relative to the mother strain, DSM 18775. It was decided to continue with one of the two mutants, TpG57 (DSM 32591).

Example 3

Detection of the Antimicrobial Product of Mutants Having an Extended Lag Phase at 30° C.

Bacteriocin Activity Test

The bacteriocin sensitive indicator strain, *Micrococcus luteus* DSM 1790, was amplified by incubation at 30° C. in BHI (BD) broth under vigorous shaking (125 rpm). To test for production of bacteriocins, a 2-fold dilution series of the supernatants of pre-cultures (spent medium) was made in MTP and an aliquot of these dilutions (50 μl) was applied to the indicator strain, *Micrococcus luteus* DSM 1790. The optical density [OD] at 600 nm was recorded every 30 minutes over a period of 20 hours at 30° C. Activity is reported in arbitrary units (AU/ml) (Table 1), and defined as the reciprocal of the highest two-fold dilution showing 50% growth inhibition of the sensitive strain.

Results

The results provided in Table 1 show the inhibition of the bacteriocin-sensitive strain, *Micrococcus luteus* (DSM1790), with spent medium from *Lactobacillus curvatus* strains DSM 32590 and DSM 18775 and by positive control *Pediococcus acidilactici* DSM 10313 grown for 20 hours at 20° C. $OD_{600}$ is the cell density of *Micrococcus* after incubation with various dilutions of spent medium (bacteriocin).

TABLE 1

| Dilution factor of spent medium | $OD_{600}$ after 20 hours growth | | |
|---|---|---|---|
| | DSM 32590 | DSM 18775 | DSM 10313 |
| Undiluted | 0 | 0 | 0 |
| 1/2 | 0 | 0.216 | 0 |
| 1/4 | 0 | 0.483 | 0 |
| 1/8 | 0 | 0.612 | 0 |
| 1/16 | 0 | 0.713 | 0 |
| 1/32 | 0 | 0.734 | 0 |
| 1/64 | 0 | 0.744 | 0 |
| 1/128 | 0.256 | 0.744 | 0.309 |
| 1/256 | 0.554 | 0.743 | 0.679 |
| 1/512 | 0.677 | 0.732 | 0.703 |
| 1/1024 | 0.677 | 0.732 | 0.707 |
| No Bacteriocin | 0.698 | 0.732 | 0.698 |
| Activity of the sample (AU/ml) | 2560 | 40 | 2560 |

The assay for production of bacteriocin demonstrated that the TS strain produced substantially more bacteriocin than the mother strain DSM 18775 over a period of 20 hours at 20° C. For DSM 32590 and DSM 10313 (a bacteriocin positive control strain) 50% inhibition was recorded at 1/128-fold dilution over a "no bacteriocin" sample without spent medium added to the *Micrococcus luteus* DSM 1790 inoculate. In Table 1 DSM 18775 shows 50% inhibition at 1/2-fold dilution with a total of 40 AU/ml [2/0.05]. The AU/ml for TpG3 was recorded to 2560 AU/ml [128/0.05]. Thus the activity for TpG3 is recorded 64-fold higher than the mother strain [AU-TpG3/AU-DSM 18775=2560/40=64].

Example 4

Challenge Test of TpG3 and TpG57 on Cooked Ham

TpG3 and TpG57 were tested to check both strains in regard to their ability to inhibit *Listeria* spp. as well as sensorial attributes and benefit on the shelf-life of cooked ham.

Preparation of the *Listeria innocua* Pre-Culture

The *L. innocua* strain which was used for the preparation of the spraying culture for inoculation was stored at −50° C.

3 days before the start of the challenge test one cryobead of the *L. innocua* strain was put into a tube which contained 9 ml BHI medium and was incubated at 37° C. overnight. The following day 0.1 ml of the overnight culture was transferred into 9 ml fresh BHI medium and incubated at 37° C. overnight. The following morning the pre-culture was stored at 4° C. until use. In the meantime, the *L. innocua* cell count of the final pre-culture was enumerated on ALOA agar. The plate was incubated at 37° C. overnight and enumerated for calculation of the cell count of the spraying solution to be used.

Preparation of the *Lactobacillus curvatus* Pre-Cultures

Pre-cultures of TpG3 and TpG57, respectively, were prepared in 150 ml MRS medium and incubated at 30° C. overnight (without shaking). The active cell count of the overnight cultures was enumerated with a flow-cytometer and an appropriate dilution made in salt-peptone solution in order to obtain a spraying solution.

Samples 100 g of sliced cooked ham was packed into a vacuum pouch for preparation of a sample. All pouches were inoculated by spraying on the surface of the cooked ham slices with 100 cfu/g of *Listeria innocua* and with one of the test strains (except for the control batch) in a cell count of 1.0E+07 cfu/g or 1.0E+05 cfu/g as follows:

Batch 1—Control

Batch 2—*Lactobacillus curvatus* DSM 18775 (1.0E+07 cfu/g)

Batch 3—TpG3 (1.0E+07 cfu/g)

Batch 4—TpG57 (1.0E+07 cfu/g)

Batch 5—TpG3 (1.0E+05 cfu/g)

Batch 6—TpG57 (1.0E+05 cfu/g)

Then the vacuum pouches were packed under modified atmosphere (70% $N_2$/30% $CO_2$) and stored at +7° C. for at least 28 days.

Analyses

*Listeria* spp. enumeration and pH measurement of each batch were carried out each week in triplicate. Both total cell count enumeration as well as lactic acid bacteria enumeration was carried out each second week also in triplicate. Cell count of the test strains was enumerated on MRS agar and the *Listeria* cell count was enumerated on ALOA agar in accordance with the corresponding ISO methods (Total plate count: ISO 4833-2:2013, Lactic acid bacteria: 15015214: 1998, *Listeria* spp.: ISO 11290-2:2017). In order to measure the pH-value of the cooked ham the sample material was grinded and homogenized with a household mixer (Moulinette from Moulinex). Furthermore, a sensorial evaluation with focus on smell and taste of the samples was done every week in addition and to support the microbiological analyses.

Results

The results of the pH evolution of the cooked ham samples, the total cell count, the lactic acid bacteria cell count and the *Listeria* spp. cell count are provided in FIGS. 3 to 6.

The results of the sensorial assessment of the cooked ham samples (n=2) during storage at +7° C. is provided in Table 2.

TABLE 2

| Batch | Strain | Day 0 Taste | Day 0 Smell/Odor | Day 7 Taste | Day 7 Smell/Odor | Day 14 Taste | Day 14 Smell/Odor | Day 21 Taste | Day 21 Smell/Odor | Day 28 Taste | Day 28 Smell/Odor |
|---|---|---|---|---|---|---|---|---|---|---|---|
| 1 | Control | ok | ok | ok | Ok | still ok | 1 ok/ 2 bad | old | Old | old | old |
| 2 | DSM18775 | ok | ok | ok | Ok | still ok | slightly sour | slightly sour | still ok | sour | sour |
| 3 | TpG3 (1.0E+07 cfu/g) | Ok | ok | ok | ok/more intensive | ok | Ok | ok | slightly sour | sour | sour |
| 4 | TpG57 (1.0E+07 cfu/g) | Ok | ok | ok | slightly sour | ok | not good | bitter | slightly sour/fresh | slightly sour/dry | slightly sour/fresh |
| 5 | TpG3 (1.0E+05 cfu/g) | Ok | ok | ok/ less taste | Ok | ok | ok/ more taste | taste+/ juicy | Ok | slightly sour/fresh | ok |
| 6 | TpG57 (1.0E+05 cfu/g) | Ok | ok | slightly sour | Ok | ok | Ok | ok | ok/slightly sour | slightly sour | slightly sour |

CONCLUSION

Figure 5:
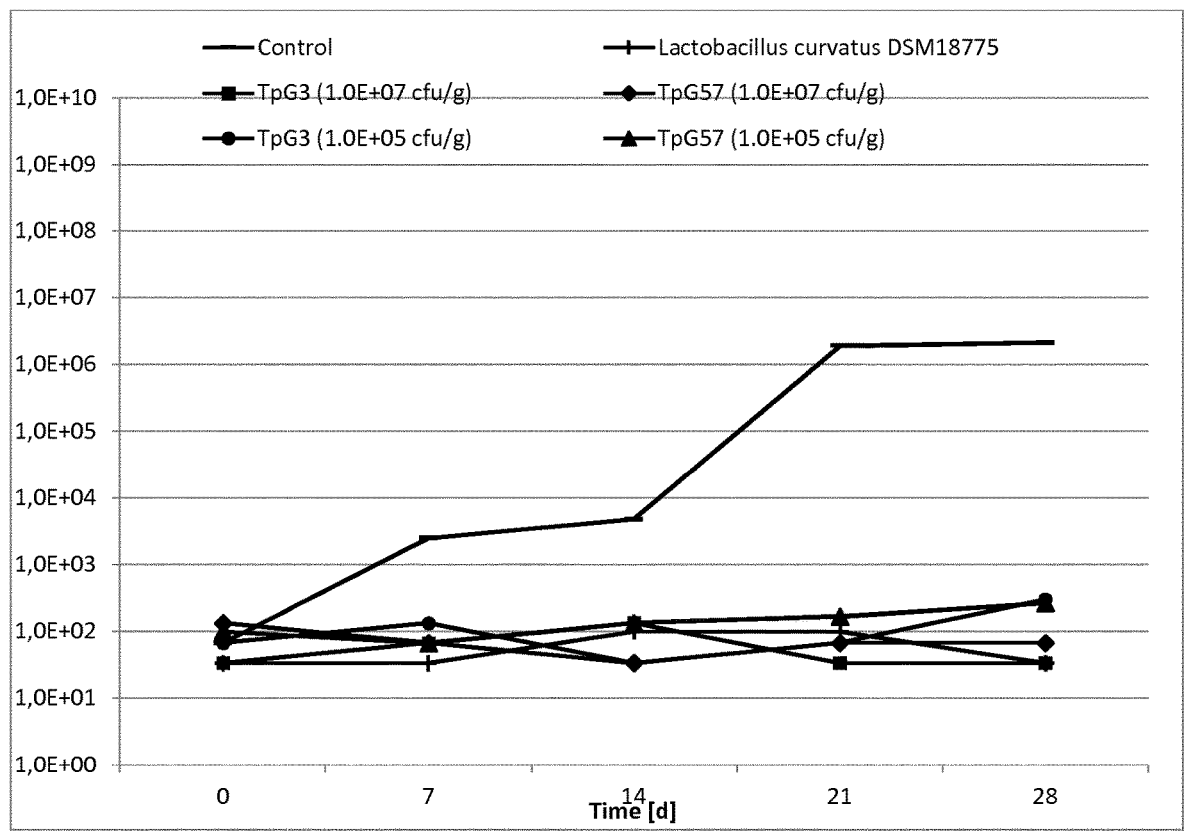

In all samples where TpG3 or TpG57 were applied, the flora of lactic acid bacteria was homogeneous and the corresponding strain was identified by its morphology with high probability. All batches reached a cell count of 1.0E+08-1.0E+09 cfu/g after 28 days at 7° C., also the batches with an inoculation level of 1.0E+05 cfu/g as well as the control batch. In regard to the inhibition effect on *Listeria* spp. no significant differences between the batches were observed. It is noteworthy that the batches with a lower inoculation level of 1.0E+05 cfu/g show an equal inhibition effect on the growth of *Listeria* spp. as the batches with an inoculation cell count of 1.0E+07 cfu/g. The *Listeria* spp. cell count of all batches to which TpG3 or TpG57 was applied stayed around the detection limit of 1.0E+02 cfu/g during the whole challenge test, whereas the *Listeria* spp. cell count of the control batch increased to approx. 1.0-5.0E+06 cfu/g after 28 days (FIG. 5).

The pH drop of the batches with the lower inoculation level of 1.0E+05 cfu/g was slower compared to the batches with the high inoculation cell count of 1.0E+07 cfu/g and reached a slightly higher pH-value after 28 days. Maybe due to the slower acidification and the slightly higher final pH-value of the batches inoculated with 1.0E+05 cfu/g, only less sensorial deviation respectively negative impact on sensorial characteristics of the product was observed during the whole challenge test (FIG. 2). Sensory-wise the TpG3 batch with an initial cell count of 1.0E+05 cfu/g gave the best results followed by the batch of TpG57 with an initial cell count of 1.0E+05 cfu/g and also the batch with TpG3 with a cell count of 1.0E+07 cfu/g was sensorially acceptable till day 28, the end of the study (Table 2).

Summarizing, when applying the mutants with an initial cell count of 1.0E+05 cfu/g the pH drop of the batches was slower and reached a slightly higher pH-value after 28 days which resulted in less negative impact on the sensorial characteristics of the product. These batches were sensory-wise much better than the ones with a higher inoculation cell count as well as both the batch inoculated with DSM 18775 and the control batch and nonetheless the inhibition effect on the growth of *Listeria* spp. was as good as for the batches inoculated with 1.0E+07 cfu/g.

The invention claimed is:

1. An isolated mutant *Lactobacillus curvatus* strain which is a mutant of the *Lactobacillus curvatus* strain deposited at the Deutsche Sammlung von Mikroorganismen and Zellkulturenwherein (DSMZ) under accession number DSM 18775, wherein the strain has an extended lag phase of at least 24 hours at 30° C. on MRS agar plates relative to strain DSM 18775 when assessed under identical conditions.

2. A mutant *Lactobacillus curvatus* strain according to claim 1, wherein the extended lag phase is extended by at least 48 hours relative to strain DSM 18775.

3. A mutant *Lactobacillus curvatus* strain according to claim 1, deposited at the DSMZ under accession number DSM 32590.

4. A mutant *Lactobacillus curvatus* strain according to claim 1, deposited at the DSMZ under accession number DSM 32591.

5. A composition comprising bacteria of a mutant *Lactobacillus curvatus* strain according to claim 1.

6. The composition according to claim 5, comprising bacteria of the mutant *Lactobacillus curvatus* strain DSM 32590 and bacteria of the mutant *Lactobacillus curvatus* strain DSM 32591.

7. The composition according to claim 5, wherein the mutant *Lactobacillus curvatus* strain is present in the composition at a concentration of at least $10^5$ CFU/g.

8. The composition according to claim 5, wherein the bacteria of the mutant *Lactobacillus curvatus* strain are the only bacteria present in the composition.

9. The composition according to claim 5, wherein the composition further comprises bacteria of one or more species selected from *Pediococcus acidilactici*, *Lactobacillus sakei*, *Lactococcus lactis*, *Leuconostoc carnosum*, and *Staphylococcus carnosus*.

10. The composition according to claim 9, wherein the bacteria of one or more of the species selected from *Pediococcus acidilactici*, *Lactobacillus sakei*, *Lactococcus lactis*, *Leuconostoc carnosum*, and *Staphylococcus carnosus* is selected from *Pediococcus acidilactici* deposited at the DSMZ under accession number DSM 28307, *Lactobacillus sakei* deposited at the DSMZ under accession number DSM 14022, *Lactococcus lactis* deposited at the DSMZ under accession number DSM 11037, and *Leuconostoc* carnosum LC1043.

11. A method for inhibiting the amount of spoilage or pathogenic bacteria in a food product, comprising adding bacteria of a mutant *Lactobacillus curvatus* strain according to claim 1 to a food product at a concentration of at least $10^5$ CFU/g.

12. The method according to claim 11, wherein the pathogenic bacteria is *Listeria*.

13. A method for inhibiting the amount of spoilage or pathogenic bacteria in a food product, comprising adding a composition according to claim 5 to a food product in an amount to provide the mutant *Lactobacillus curvatus* strain at a concentration of at least $10^5$ CFU/g.

14. The method according to claim 13, wherein the pathogenic bacteria is *Listeria*.

15. A mutant *Lactobacillus curvatus* strain according to claim 1, wherein the strain is a bacteriocin-producing strain.

16. A composition comprising bacteria of a mutant *Lactobacillus curvatus* strain according to claim 15.

17. A method for inhibiting the amount of spoilage or pathogenic bacteria in a food product, comprising adding bacteria of a mutant *Lactobacillus curvatus* strain according to claim 15 to a food product at a concentration of at least $10^5$ CFU/g.

* * * * *